(12) United States Patent
Ryan et al.

(10) Patent No.: US 6,914,057 B1
(45) Date of Patent: Jul. 5, 2005

(54) INHIBITOR OF CATARACT FORMATION

(75) Inventors: Maria Emanuel Ryan, Huntington, NY (US); Lorne M. Golub, Smithtown, NY (US); Nungavaram S. Ramamurthy, Smithtown, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/787,866

(22) PCT Filed: Sep. 28, 1999

(86) PCT No.: PCT/US99/22354

§ 371 (c)(1),
(2), (4) Date: Mar. 22, 2001

(87) PCT Pub. No.: WO00/18353

PCT Pub. Date: Apr. 6, 2000

Related U.S. Application Data

(60) Provisional application No. 60/102,056, filed on Sep. 28, 1998.

(51) Int. Cl.[7] ............................................. A61K 31/65
(52) U.S. Cl. ........................................................ 514/152
(58) Field of Search ................................... 514/152, 912

(56) References Cited

U.S. PATENT DOCUMENTS

| | | | |
|---|---|---|---|
| 5,244,673 A | 9/1993 | Gejkova et al. | |
| 5,474,764 A | 12/1995 | Patel et al. | |
| 5,814,655 A | 9/1998 | Patel et al. | |
| 5,929,055 A | 7/1999 | Ryan et al. | |

OTHER PUBLICATIONS

HCAPLSU, DN 76:30596, (1972), abstract for Smirnov, Makro–Mikrostrukt. Tkanei Norme, Pato.. Eksp. (1969), 34–43.*

Patent Abstracts of Japan, vol. 1998, Pub. No. 09315954 (Sep. 12, 1997).

Chemical Abstracts, vol. 93, No. 7, 1980, Columbus, Ohio, US; Abstract No. 60992e, p. 27, XP002294479.

Ryan, M, R. et al. "MMP–mediated Events in Diabetes," Reprinted from Inhibition of Matrix Metalloproteinases, *Annuals of the New York Academy of Sciences* 878:311–334 (1999).

Butcher, J.M., et al. "Bilateral cataracts and glaucoma induced by long term use of steroid eye drops," *British Medical Journal* 309(6946):43 (1994).

* cited by examiner

*Primary Examiner*—Phyllis G. Spivack
(74) *Attorney, Agent, or Firm*—Hoffman & Baron, LLP

(57) ABSTRACT

Methods of reducing the risk of cataract development in a mammal are provided and include administering to the mammal an effective amount of a tetracycline derivative. A preferred tetracycline derivative administered according to the methods of the present invention is 6α-deoxy 5-hydroxy-4-dedimethylaminotetracycline.

25 Claims, 3 Drawing Sheets

INHIBITOR OF CATARACT FORMATION

CROSS-REFERENCE TO RELATED APPLICATIONS

This application is the National Stage of PCT Application No. PCT/US99/22354, filed Sep. 28, 1999, which claims priority to U.S. Provisional Application No. 60/102,056, filed Sep. 28, 1998. The entire disclosure of the aforementioned applications are incorporated herein by reference.

This invention was made with support from the United States government. The United States government has certain rights in this invention.

BACKGROUND OF THE INVENTION

Cataracts are an abnormal progressive condition of the lens of the eye, characterized by loss of transparency. A gray-white opacity can be seen within the lens, behind the pupil. Most cataracts are caused by degenerative changes, occurring most often after fifty years of age, however in susceptible patients such as diabetics, cataracts can occur at a much earlier age.

Two types of cataracts have been described: (1) metabolic or juvenile cataracts, which are observed in children and young adults with uncontrolled diabetes, and (2) senile cataracts which are more common than metabolic cataracts. The cataracts in diabetics are similar to the senile cataracts observed in non-diabetic patients but tend to occur at a younger age (e.g. the aging process is accelerated).

The tendency to develop cataracts is inherited and can be accelerated by diseases such as diabetes. If cataracts are untreated, sight is eventually lost. First, vision is blurred, then bright lights glare diffusely, and finally, distortion and double vision may develop.

Previously, cataracts have been treated according to the progressive condition of the lens of the eye. In particular, senile cataracts are usually treated with excision of the lens and prescription of special contact lenses or glasses. The soft cataracts of children and young adults can either be incised and drained or fragmented by ultrasound, followed by irrigation and aspiration of the fragments through a minute incision.

As stated above, the tendency to develop cataracts is inherited and can be accelerated by diseases such as diabetes. Diabetes is the leading cause of blindness in adults and accounts for loss of vision in 8% of those who are legally blind in the United States (Klein and Klein, 1995). Sixty-five percent of diabetic patients develop blindness within five years after detection of proliferative retinopathy (Lavine, 1990). An additional complication of diabetes in the eye is associated with swelling of the lens. This swelling is a result of the accumulation of fructose and sorbitol that increases the osmolality within the lens. As this process continues, lens protein becomes denatured and cataracts form (Lavine, 1990).

Studies of the blood vessels in the eve of an animal model of Type II diabetes, the ZDF/Gmi-fa rat, have demonstrated microscopic vascular changes in the retina, such as an increase in capillary nuclear density and an increase in basement membrane thickness, when compared to non-diabetic control animals (Danis et al., 1993). Danis et al, demonstrated that these animals develop microvascular retinopathy determined morphologically by increases in the numbers of endothelial cells (endothelial hyperplasia) and associated capillaries. A prominent early marker for diabetic retinopathy is pericyte degeneration and the development of pericyte ghosts. Another eye complication seen in this diabetic rat model is the development of cataracts.

Using compounds approved for use in humans and available in the oral. injectable and topical routes, such as tetracycline, to treat diseases or conditions such as cataracts has not been suggested. The compound, tetracycline, exhibits the following general structure:

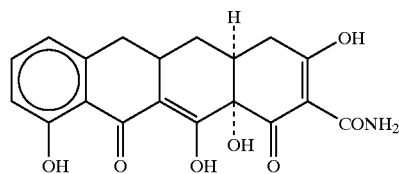

The numbering system of the ring nucleus is as follows:

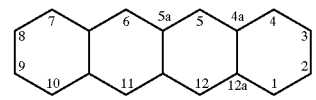

Tetracycline as well as the 5-OH (Terramycin) and 7-Cl (Aureomycin) derivatives exist in nature, and are well known antibiotics. Natural tetracyclines can be modified without losing their antibiotic properties, although certain elements of the structure must be retained. The modifications that can and cannot be made to the basic tetracycline structure have been reviewed by Mitscher in *The Chemistry of Tetracyclines*, Chapter 6, Miarcel Dekker, Publishers, New York (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antimicrobial activity. An example of a chemically modified tetracycline (hereinafter CMT) is 4-dedimethylaminotetracyline which is commonly considered to be a non-antimicrobial tetracycline.

In addition to their antibiotic properties, tetracyclines have been described as having a number of other uses. For example, tetracyclines are also known to inhibit the activity of collagen destructive enzymes such as mammalian collagenase, gelatinase, macrophage elastase and bacterial collagenase. Golub et al., *J. Periodoat. Res.* 20:12–23 (1985); Golub et al. *Crit. Revs. Oral Biol. Med.* 2: 297–322 (1991);U.S. Pat. Nos. 4,666,897; 4,704,383; 4,935,411; 4,935,412. In addition, tetracyclines have been known to inhibit wasting and protein degradation in mammalian skeletal muscle, U.S. Pat. No. 5,045,538.

Furthermore, tetracyclines have been shown to enhance bone protein synthesis in U.S. Pat. No. Re. 34,656 and to reduce bone resorption in organ culture in U.S. Pat. No. 4,704,383.

Similarly, U.S. Pat. No. 5,532,227 to Golub et al., discloses that tetracyclines can ameliorate the excessive glycosylation of proteins. In particular, tetracyclines inhibit the excessive collagen cross linking which results from excessive glycosylation of collagen in diabetes.

These properties cause tetracyclines to be useful in treating a number of diseases. For example, there have been a number of suggestions that tetracyclines, including non-antimicrobial tetracyclines, are effective in treating arthritis. See, for example, Greenwald et al., "Tetracyclines Suppress Metalloproteinase Activity in Adjuvant Arthritis and, in Combination with Flurbiprofen. Ameliorate Bone Damage," *Journal of Rheumatology* 19:927–938(1992); Greenwald et al., "Treatment of Destructive Arthritic Disorders with MMP Inhibitors: Potential Role of Tetracyclines in, Inhibition of Matrix Metalloproteinases: Therapeutic Potential," *Annals of the New York Academy of Sciences* 732: 181–198 (1994); Kloppenburg et al., "Minocycline in Active Rheumatoid Arthritis," *Arthritis Rheum* 37:629–636(1994); Ryan et al., "Potential of Tetracycline to Modify Cartilage Breakdown in Osteoarthritis," *Current Opinion in Rheumatology* 8: 238–247(1996); O'Dell et al., "Treatment of Early Rheumatoid Arthritis with Minocycline or Placebo," *Arthritis Rheum* 40:842–848(1997)., Tetracyclines have also been suggested for use in treating skin diseases. For example, White et al., *Lancet*, April 29, p. 966 (1989) reports that the tetracycline minocycline is effective in treating dystrophic epidermolysis bullosa, which is a life-threatening skin condition believed to be related to excess collagenase.

The effectiveness of tetracycline in skin disorders has also been studied by Elewski et al., *Journal of the American Academy of Dermatology* 8:807–812 (1983). Elewski et al. disclosed that tetracycline antibiotics may have anti-inflammatory activity in skin diseases.

Similarly, Plewig et al., *Journal of Investigative Dermatology* 65:532 (1975), disclose experiments designed to test the hypothesis that antimicrobials are effective in treating inflammatory dermatoses. The experiments of Plewig et al. establish that tetracyclines have anti-inflammatory properties in treating pustules induced by potassium iodide patches.

The use of tetracyclines in combination with non-steroidal anti-inflammatory agents has been studied in the treatment of inflammatory skin disorders caused by acne vulgaris. Wong et al., *Journal of American Academy of Dermatology* 1: 1076–1081 (1984), studied the combination of tetracycline and ibuprofen and found tetracycline to be an effective agent against acne vulgaris and ibuprofen to be useful in reducing the resulting inflammation by inhibition of cycloxygenase. Funt et al., *Journal of the American Academy of Dermatology* 13: 524–525 (1985), disclosed similar results by combining antimicrobial doses of minocycline with ibuprofen.

An antimicrobial tetracycline derivative, doxycycline, has been used to inhibit nitrate production. D'Agostino et al., *Journal of Infectious Diseases*: 177:489–92 (1998), discloses experiments where doxycycline, administered to mice injected with bacterial lipopolysaccharide (hereinafter LPS), exerted a protective effect by inhibiting nitrate production by an IL-10 independent mechanism. Experiments carried out in vitro also showed that doxycycline inhibited nitric oxide synthesis by LPS activated macrophages without enhancing endogenous IL-10 release.

Based on the foregoing, tetracyclines have been found to be effective in different treatments. However, there has been no suggestion whatsoever that tetracyclines can be used to reduce the risk of cataract development in a mammal.

Accordingly, it is one of the purposes of this invention, among others, to provide an economical and relatively uncomplicated method of reducing the risk of cataract development.

SUMMARY OF THE INVENTION

It has now been discovered that these and other purposes can be achieved by the present invention, which provides for methods of reducing the risk of cataract development in a mammal.

The methods of the present invention provide for reducing the risk of cataract development in a mammal by administering to the mammal an effective amount of a tetracycline derivative. A preferred method of the present invention provides that the tetracycline derivative is a non-antimicrobial tetracycline.

Another preferred method of the present invention provides for reducing the risk of cataract development by administering to a mammal an effective amount of a chemically-modified tetracycline derivative, for example dedimethylaminotetracycline. A preferred dedimethylaminotetracycline derivative is 6α-deoxy 5-hydroxy 4-dedimethylaminotetracycline (CMT-8).

Other dedimethylaminotetracyclines which can be administered according to the methods of the present invention include 4dedimethylaminotetracycline, 4-dedimethylamino-5-oxytetracycline, 4-dedimethylamino-7-chlorotetracycline, 4-hydroxy-4-dedimethylaminotetracycline, 5a, 6-anhydro-4-hydroxy-4-dedimethylaminotetracycline, 6α-deoxy-5-hydroxy-4-dedimethylaminotetracycline, 6-demethyl-6-deoxy-4-dedimethylaminotetracycline, 4-dedimethylamino-12a-deoxytetracycline, 12α-deoxy-4-deoxy-4-dedimethylaminotetracycline, 12a, 4α-anhydro-4-dedimethylaminotetracycline, 7-dimethylamino-6-demethyl-6-deoxy-4-dedimethylaminotetracycline, 5-hydroxy-6-α-deoxy-4-dedimethylaminotetracycline, 4-dedimethylamino-12α-deoxyanhydrotetracycline and 4-dedimethylamino-11-hydroxy-12a-deoxytetracycline.

Other dedimethylaminotetracyclines which can be administered according to the methods of the present invention have D ring substituents at the C7 and/or C9 positions on the 4-dedimethylaminotetracycline molecule, These compounds include 7-azido-6-demethyl-6-deoxy4-dedimethylamino tetracycline, 7-dimethylamino-9-azido-6-demethyl-6-deoxy4-dedimethylamino tetracycline, 9-amino-6-demethyl-6-deoxy4-dedimethylaminotetracycline, 9-azido-6-demethyl-6deoxy-4-dedimethylaminotetracycline, 9-nitro-6-demethyl-6-deoxy-4-dedimethylaminotetracycline, 9-amino-7-dimethylamino-6-demethyl-6-deoxy-4-dedimethylaminotetracycline, 7-acetamido-6-demethyl-6-deoxy-4-dedimethylamino tetracycline, 9-acetamido-6-demethyl-6-deoxy-4-dedimethylaminotetracycline, 7-amino-9-nitro-6-demethyl-6-deoxy-4-dedimethylaminotetracycline, 9-(N,N,-dimethyl) glycylamino-6-demethyl-6-deoxy-4-dedimethylaminotetracycline, 7, 9-diamino-6-demethyl-6-deoxy4-dedimethylaminotetracycline, 9-ethoxythiocarbonylthio-6-demethyl-6-deoxy-4-dedimethylaminotetracycline, 7-dimethylamino-9-acetamido-6-demethyl-6-deoxy-4-dedimethyl aminotetracycline, 9-azido-7-dimethylamino-6-demethyl-6-deoxy-4-dedimethylaminotetracycline, 9-azido-7-dimethylamino-6-demethyl-6-deoxy-4-dedimethylaminotetracycline, 7-azido-5-hydroxy-6-deoxy-4-dedimethylamino tetracycline, 7-dimethylamino-9-azido-5-hydroxy-6-deoxy-4-dedimethylamino tetracycline, 9-amino-5-hydroxy-6-deoxy-4-dedimethylaminotetracycline, 9-azido-5-hydroxy-6-deoxy-4-dedimethylaminotetracycline, 9-nitro-5-hydroxy-6-deoxy-4-dedimethylaminotetracycline, 9-amino-7-dimethylamino-5-hydroxy-6-deoxy-4-dedimethylaminotetracycline, 7-acetamido-5-hydroxy-6-deoxy-4-dedimethylamino tetracycline, 9-acetamido-5-hydroxy-6-deoxy-4-dedimethylaminotetracycline, 7-amino-9-nitro-5-hydroxy-6-deoxy4-dedimethylaminotetracycline, 9-(N,N-dimethyl) glycylamino-5-hydroxy-6-deoxy-4-dedimethylaminotetracycline, 7, 9-diamino-5-hydroxy-6- deoxy-4dedimethylaminotetracycline, 7-dimethylamino-9-amino-5-hydroxy-6-deoxy-4-dedimethylaminotetracycline, 9-ethoxythiocarbonylthio-5-hydroxy-6-deoxy-4-dedimethylaminotetracycline, 7-dimethylamino-9-acetamido-5-hydroxy-6-deoxy-4-dedimethylaminotetracycline, 9-azido-7-dimethylamino-5-hydroxy-6-deoxy-4-dedimethylaminotetracycline, 9-amino-8-chloro-5-hydroxy-6-deoxy-4-dedimethylaminotetracycline, 9-(N,N-dimethyl) glycylamino-5-hydroxy-6-deoxy-4-dedimethylaminotetracycline, 9-nitro-7-dimethylamino-6-demethyl-6-deoxy-4-dedimethylaminotetracycline, 9-acetamido-7-dimethylamino-6-demethyl-6-deoxy-4-dedimethylaminotetracycline, 9-(N, N-dimethyl) glycylamino-7-dimethylamino-6-demethyl-6-deoxy4-dedimethylaminotetracycline, and 9-ethoxythiocarbonylthio-7-dimethylamino-6demethyl-6-deoxy-4-dedimethylaminotetracycline.

In addition, the D ring may be halogenated at the C8 position to provide 8-halo-dedimethylaminotetracycline derivatives. As used in this specification, halogens can be chlorine, fluorine, bromine, and iodine. Some examples of 8-halo-dedimethylaminotetracycline derivatives are 9-amino-8-chloro-7-dimethylamino-6-demethyl-6-deoxy4-dedimethylaminotetracycline, 9-amino-8-chloro-7-dimethylamino-5-hydroxy-6-deoxy4-dedimethylaminotetracycline and 9-amino-8-chloro-6-demethyl-6-deoxy-4dedimethylaminotetracycline.

Another preferred method of the present invention provides for reducing the risk of cataract development in a mammal by administering a tetracycline derivative selected from the group consisting of 6a-benzylthiomethylenetetracycline, tetracyclinotrile, the mono-N-alkylated amide of tetracycline, 6-fluoro-6-demethyltetracycline, 11a-chlorotetracycline, tetracycline pyrazole and 12a-deoxytetracycline and its derivatives.

Another preferred method of the present invention provides that the tetracycline derivative is an antimicrobial tetracycline. Antimicrobial tetracycline derivatives which can be used with the methods of the present invention include tetracycline, minocycline and doxycycline.

Another method of the present invention provides for reducing the risk of cataract development in a mammal by administering a tetracycline derivative systemically. Preferably, the tetracycline derivative is administered systemically by a controlled release delivery system. Additional methods of the present invention provide for reducing the risk of cataract development in a mammal by administering a tetracycline derivative orally or topically.

These and other advantages of the present invention will be appreciated from the detailed description and drawings which are set forth herein. The detailed description and the drawings enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein.

DETAILED DESCRIPTION OF THE INVENTION

Figure 1:
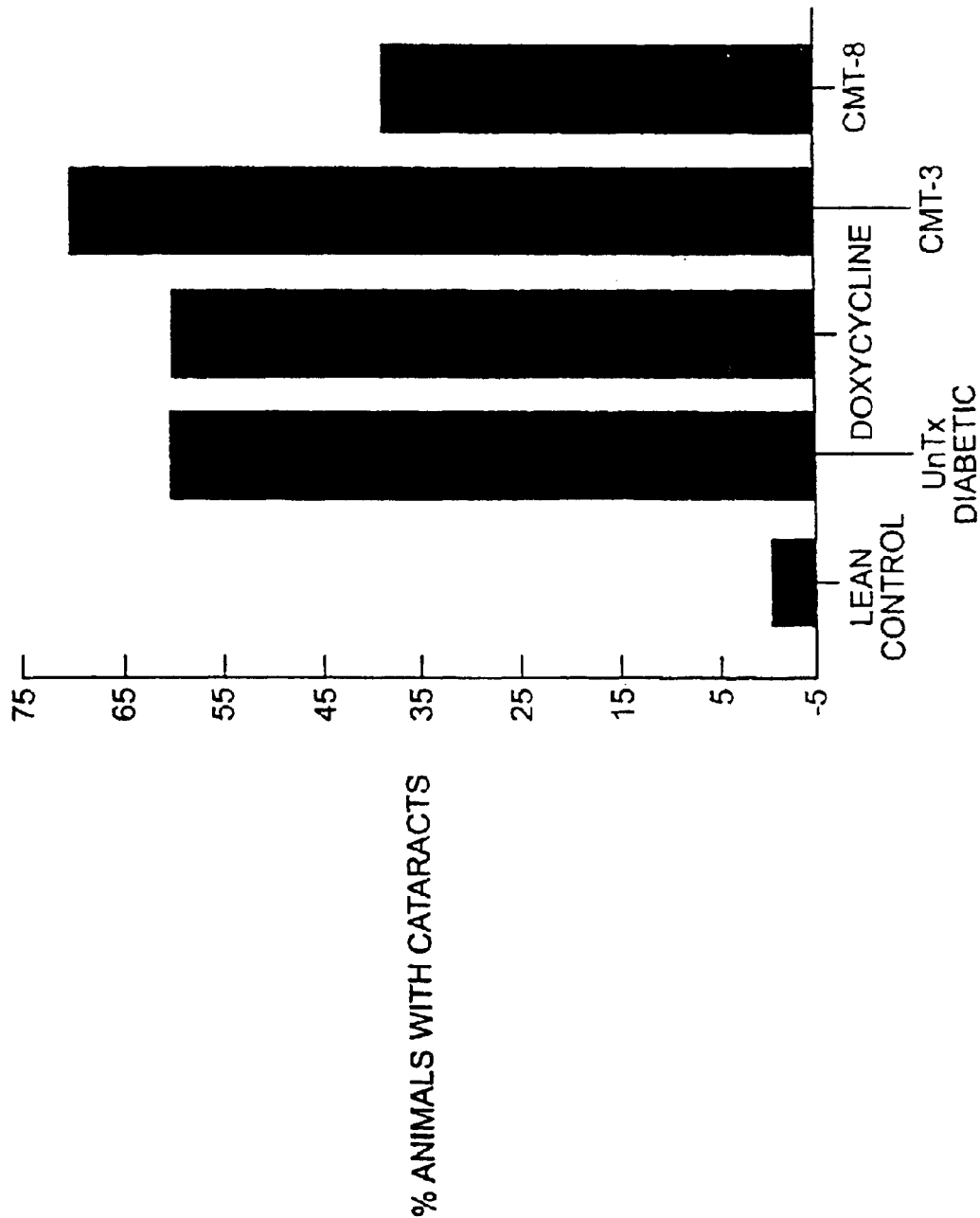
FIG. 1 is a bar graph illustration of the development of cataracts in untreated Type II ZDF/GMI diabetic rats and diabetic rats treated with doxycycline, CMT-3 (6-demethyl-6-deoxy4-dedimethylaminotetracycline) and CMT-8 (5-hydroxy-6-α-deoxy-4-dedimethylaminotetracycline).

The present invention provides for methods of reducing the risk of cataract development in a mammal. The methods provide for administering to a mammal an effective amount of a tetracycline derivative.

The methods of the present invention can be used in any living mammal. Mammals include, for example, humans, as well as pet animals such as dogs and cats, laboratory animals, such as rats and mice, and farm animals, such as horses and cows.

A tetracycline derivative as used herein, exhibits the following general ring structure:

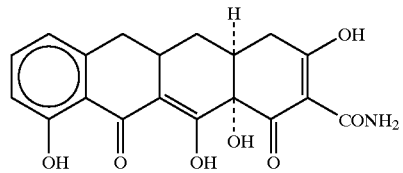

The numbering system of the multiple ring nucleus is as follows:

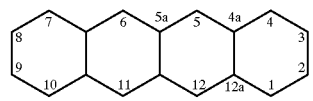

Tetracycline, as well as the 5-OH (oxytetracycline, e.g. Terramycin) and 7-Cl (chlorotetracycline, e.g., Aureomycin) derivatives, exist in nature, and are all well known antibiotics. Semisynthetic tetracyclines include, for example, doxycycline, minocycline and methacycline.

A class of compounds has been defined which are structurally related to the antibiotic tetracyclines, but which have had their antibiotic activity substantially or completely eliminated by chemical modification. Substantial elimination of antibiotic activity occurs when the antibiotic activity is substantially less than that of tetracycline. Preferably, the antibiotic activity is at least approximately two times less than that of tetracycline, more preferably at least approximately five times less than that of tetracycline, and even more preferably at least approximately ten times less than that of tetracycline.

The modifications that can and cannot be made to the basic tetracycline structure were reviewed by Mitscher, L. A., The Chemistry of the Tetracycline Antibiotics, Marcel Dekker, New York (1978), Ch. 6. According to Mitscher, the modification at positions 5–9 of the tetracycline ring system can be made without causing the complete loss of antibiotic properties. However, changes to the basic structure of the ring system, or replacement of substituents at positions 14 or 10–12, generally lead to synthetic tetracyclines with substantially less or essentially no antibacterial activity.

Chemically modified tetracyclines (CMT's) derivatives include, for example, 4-dedimethylaminotetracycline (CMT-1), tetracyclinonitrile (CMT-2), 6-demethyl-6-deoxy- 4-dedimethylaminotetracycline (CMT-3), 7-chloro-4dedimethylaminotetracycline (CMT-4), tetracyclinopyrazole (CMT-5), 4-hydroxy-4-dedimethylaminotetracycline (CMT-6), 12α-deoxy-4-dedimethylaminotetracycline (CMT-7), 5-hydroxy-6-α-deoxy-4-dedimethylaminotetracycline (CMT-8), 4-dedimethylamino-12-α-deoxyanhydrotetracycline (CMT-9) and 7-dimethylamino-6-demethyl-6-deoxy-4-dedimethylaminotetracycline (CMT-10). All are useful as non-antibacterial tetracyclines that reduce the risk of cataract development in a mammal.

A particularly preferred tetracycline derivative suitable for use according to the present invention is CMT-8.

Tetracycline derivatives which possess antibacterial activity are also contemplated by the present invention. However, such compounds are preferably employed in an amount which has substantially no antibacterial activity but which is effective for reducing the risk of cataract formation in a mammal. Preferred compounds of this type include tetracycline, minocycline and doxycycline.

The chemically modified and antimicrobial tetracycline derivatives can be made by methods known in the art. See, for example, Mitscher, L. A., The Chemistry of the Tetracycline Antibiotics, Marcel Dekker, New York (1978), Ch. 6 and U.S. Pat. Nos. 4,704,383 and 5,532,227.

According to the methods of the present invention, an effective amount of a tetracycline derivative is administered. An "effective amount" as used herein is that amount effective to achieve the specified result of reducing the risk of cataract formation. Preferably, the tetracycline derivative is provided in an amount which has little or no antimicrobial activity. A tetracycline derivative is not effectively antimicrobial if it does not significantly prevent the growth of microbes. Accordingly, the methods of the present invention can beneficially employ a tetracycline derivative which has been modified chemically to reduce or eliminate its antimicrobial properties. The use of CMT's is preferred in the present invention since they can be used at higher levels than antimicrobial tetracyclines, while avoiding certain disadvantages such as the indiscriminate killing of beneficial microbes and the emergence of resistant microbes, which often accompanies the use of antimicrobial or antibacterial amounts of such compounds.

Tetracycline derivatives which are useful according to the methods of the present invention appear to exhibit their beneficial effect in a dose-dependent manner although CMT-8 exhibits its best effect when absorbed. Thus, within broad limits, administration of larger quantities of a tetracycline derivative has been observed to further reduce the risk of cataract formation than does administration of smaller amounts. Moreover, efficacy has been observed at dosages below the level at which toxicity is seen.

Maximal dosage for a subject is the highest dosage which does not cause undesirable or intolerable side effects. For example, the tetracycline compound can be administered in an amount of from about 0.1 mg/kg/day to about 30 mg/kg/day, and preferably from about 1 mg/kg/day to about 18 mg/kg/day. For the purpose of the present invention, side effects can include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described effect.

The methods of the present invention involve administering a tetracycline derivative in an amount which is effective for reducing the risk of cataract formation in a mammal.

Administering tetracycline derivatives can be accomplished in a variety of ways. For example, tetracycline derivatives can be administered systemically by the parenteral and enteral routes, and include controlled release delivery systems. For example, a tetracycline derivative can easily be administered intravenously (e.g., intravenous injection) which is a preferred route of delivery. Intravenous administration can be accomplished by mixing the tetracycline derivative in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide a tetracycline derivative.

Alternatively, delivery of a tetracycline derivative can include topical application. Accordingly, the carrier is preferably suited for topical use. Compositions deemed to be suited for such topical use include gels, salves, lotions, creams, ointments and the like. The tetracycline derivative can also be incorporated with a support base or matrix or the like to provide a pre-packaged surgical or burn dressing or bandage which can be directly applied to skin. Topical application of tetracycline derivatives in amounts of up to about 25% (w/w) in a vehicle are therefore appropriate. More preferably, application of tetracycline derivatives in amounts of from about 0.1% to about 10% is believed to effectively reduce the risk of cataract formation according to the present invention. It is believed that these quantities do not induce significant toxicity in the subject being treated.

Combined or coordinated topical and systemic administration of tetracycline derivatives is also contemplated under the invention. For example, a non-absorbable tetracycline compound, such as CMT-2 or CMT-6, can be administered topically, while a tetracycline compound capable of substantial absorption and effective systemic distribution in a subject, such as CMT-1, CMT-3, CMT-7 or CMT-8, can be administered systemically.

The invention has been developed based on the unexpected observation by Applicants that tetracycline derivatives reduce the risk of cataract formation in a mammal. Applicants are unaware of any physiological or biochemical basis for expecting that tetracyclines would reduce the risk of cataract formation in a mammal. It is, therefore, surprising that tetracycline derivatives are found to reduce the risk of cataract formation in a mammal.

Diabetics develop posterior subcapsular cataracts, characterized by a central opacity in the nucleus and cortex. In studies on ZDF/Gmi-fa rats, for example, non-diabetic controls did not develop clinically-detectable cataracts, whereas 65% of the untreated Type II diabetic rats developed these ocular lesions by 5 months of age, an increase in incidence that was statistically significant ($p<0.001$). Of extreme interest, treatment with CMT-8 appeared to prevent the development of these cataracts at five months while the antimicrobial parent compound doxycycline was not as effective. In the current study, CMT-8 administration to the Type II diabetic rats reduced the incidence of cataract development by 37% at five months. In fact, this therapeutic effect may have been underestimated since it was an unexpected finding and, therefore, was not documented at the earlier time points. The mechanisms by which Type II (and Type I) diabetes causes the development of these cataracts is not yet understood.

Systemic administration of a tetracycline derivative such as CMT-8 should prevent the development of cataracts, which if left untreated can lead to blindness. The use of this therapeutic in individuals prone to cataract formation prophylactically could reduce the need for surgical intervention. In the case of surgical treatment, the use of CMT-8 could prevent recurrence of cataracts.

FIG. 1 shows the development of cataracts in untreated Type II ZDF/GMI diabetic rats and Type II ZDF/GMI diabetic rats treated with different tetracycline analogues. Specifically, approximately 60% of untreated Type II ZDF/GMI diabetic rats developed cataracts whereas approximately 42% of Type II ZDF/GMI diabetic rats treated with CMT-8 developed cataracts.

Type II ZDF/GMI diabetic rats treated with other tetracycline analogues did not exhibit as low a percentage of cataract development in comparison to Type II ZDF/GMI diabetic rats treated with CMT-8. In particular, approximately 60% of Type II ZDF/GMI diabetic rats treated with doxycycline developed cataracts and approximately 70% of Type II ZDF/GMI diabetic rats treated with CMT-3 developed cataracts.

It is believed that the lack of efficacy for doxycycline and CMT-3 was due to the serum concentration achieved. Doxycycline, CMT-3 and CMT-8 were each administered at an oral dose of 15 mg/kg with rat pK studies revealing that equivalent oral doses result in very different peak serum concentrations. The peak serum concentration for doxycycline was determined to be 0.9 μg/ml and the peak serum concentration for CMT-3 was determined to be 4.6 μg/ml. The peak serum concentration, though, for CMT-8 was determined to be 15 μg/ml. Liu et al., The Lipophilicity and Pharmacokdnetics of Different Chemically-Modified Tetracyclines (CMTs) In Vivo, *Current Medicinal Chemistry*, submitted for publication in September 1999. Clearly, administration of higher oral doses of CMT-3 and doxycycline would be needed to achieve serum concentrations similar to CMT-8.

Figure 2:
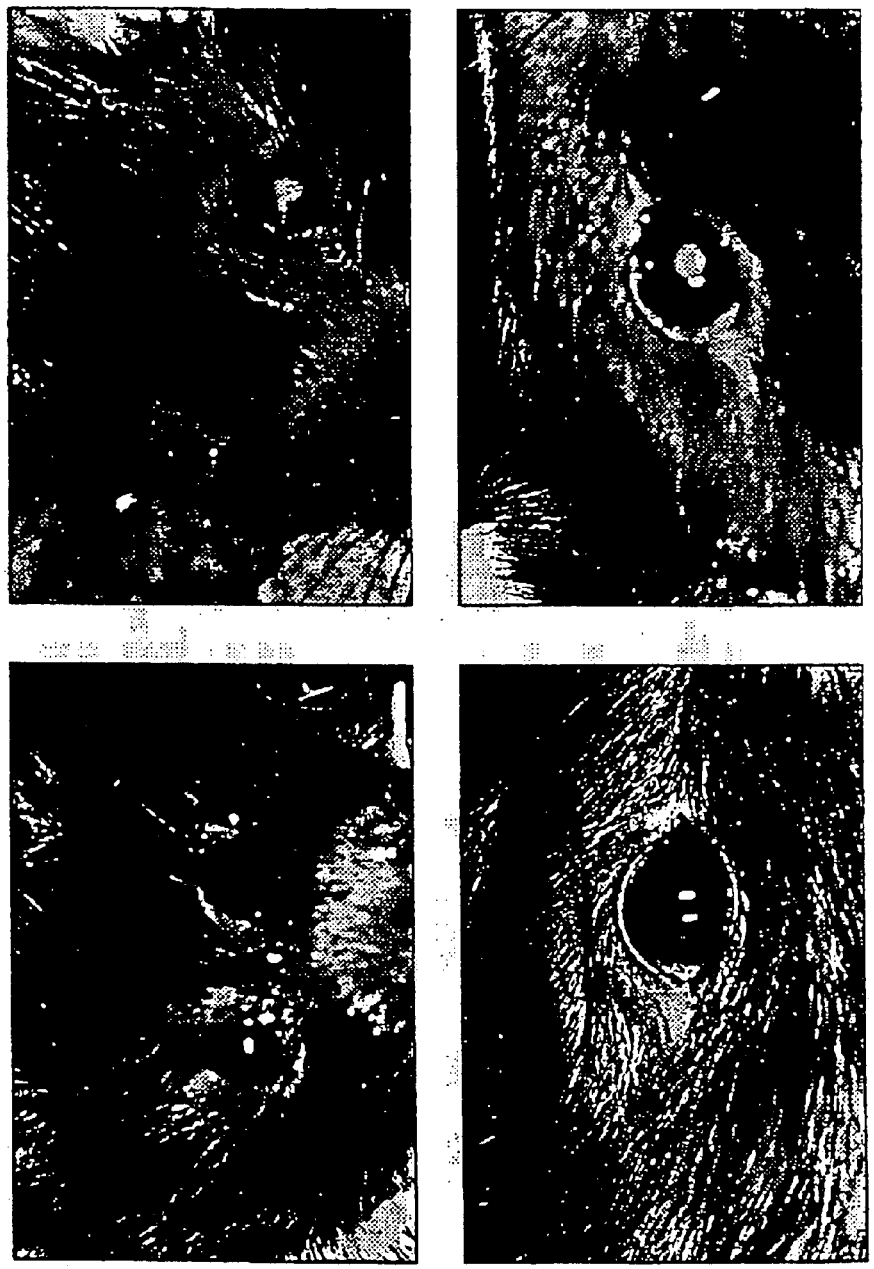
FIG. 2 is a photographic illustration of the development of cataracts in untreated Type 11 ZDF/GMI diabetic rats in comparison with healthy control rats.
Figure 3:
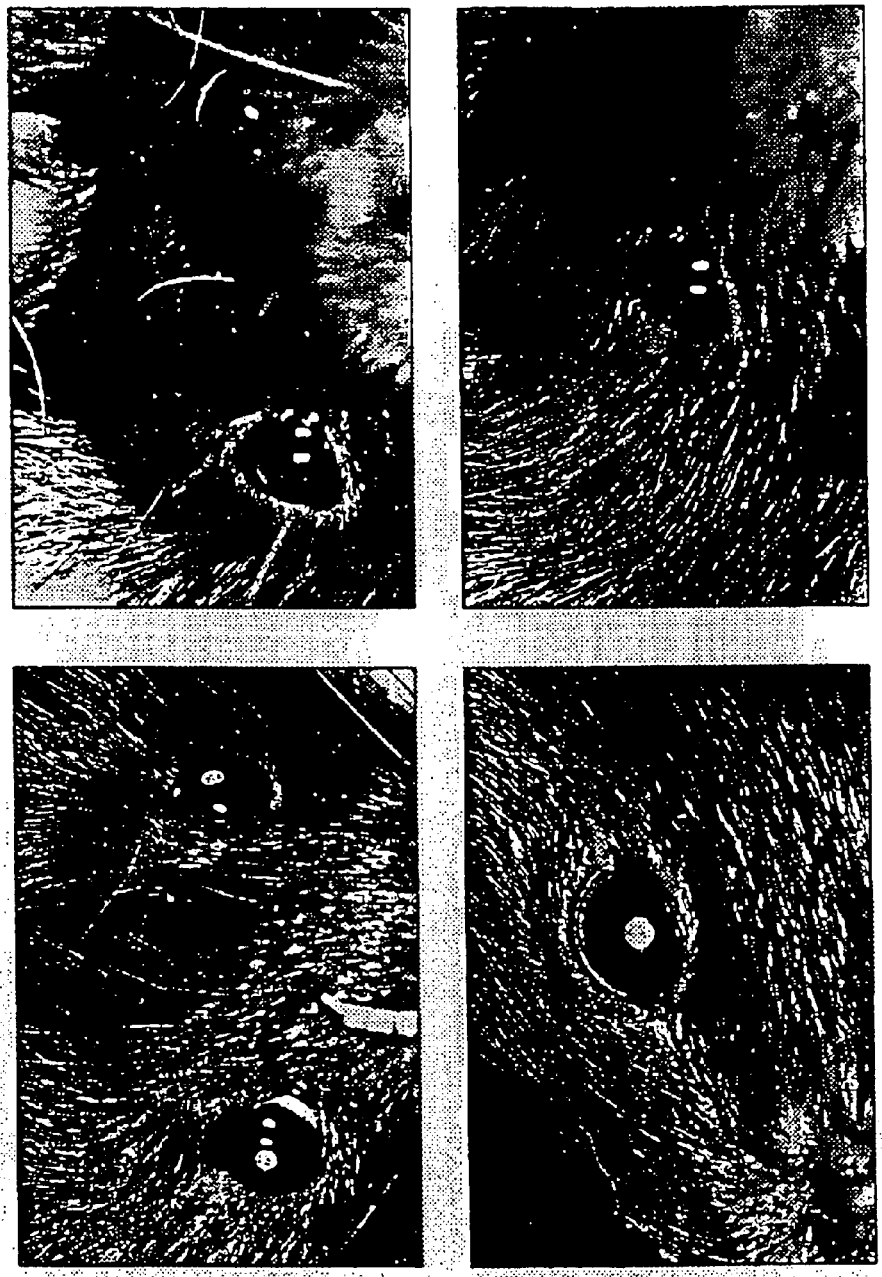
FIG. 3 is a photographic illustration of the development of cataracts in Type II ZDF/GMI diabetic rats treated with doxycycline and CMT-8.

FIGS. 2 and 3 provide a comparison of healthy untreated rats with untreated Type II ZDF/GMI diabetic rats and Type II ZDF/GMI diabetic rats treated with doxycycline and CMT-8. Cataracts do not appear to have developed in the CMT-8 treated diabetic rats as they appear very similar to the non-diabetic control rats. Treating diabetic rats with doxycycline to prevent cataract development does not appear to be effective although it is believed that the lack of efficacy was due to the low serum concentration as discussed above.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method of reducing the risk of cataract development in a mammal in need thereof comprising administering to the mammal an effective amount of a non-antibacterial tetracycline derivative, wherein the derivative has the structure of an antibiotic tetracycline in which a change to the basic structure of the ring system, or replacement of a substituent at position 1–4 or 10–12, has been made.

2. A method according to claim 1, wherein said tetracycline derivative is a dedimethylaminotetracycline.

3. A method according to claim 2, wherein said dedimethylaminotetracycline is selected from the group consisting of 4-dedimethylaminotetracycline, 4-dedimethylamino-5-oxytetracycline, 4-dedimethylamino-7-chlorotetracycline, 4-hydroxy-4-dedimethylaminotetracycline, 5 a,6-anhydro4-hydroxy4-dedimethylaminotetracycline, 6α-deoxy-5-hydroxy-4-dedimethylaminotetracycline, 6-demethyl-6-deoxy-4-dedimethylaminotetracycline, 4-dedimethylamino-12a-deoxytetracycline, 12α-deoxy-4-deoxy-4-dedimethylaminotetracycline, 12a, 4α-anhydro-4-dedimethylaminotetracycline, 7-dimethylamino-6-demethyl-6-deoxy-⁴-dedimethylaminotetracycline, 5-hydroxy-6-α-deoxy4-dedimethylaminotetracycline, 4-dedimethylamino-12α-deoxyanhydrotetracycline and 4-dedimethylamino-11-hydroxy-12a-deoxytetracycline.

4. A method according to claim 1, wherein said tetracycline derivative is 6-α-deoxy-5-hydroxy-4-dedimethylamino tetracycline.

5. A method according to claim 1, wherein said tetracycline derivative is selected from the group consisting of 6a-benzylthiomethylenetetracycline, tetracyclinotrile, the mono-N-alkylated amide of tetracycline, 6-fluoro-6-demethyltetracycline, 11a-chlorotetracycline, tetracycline pyrazole, and 12a-deoxytetracycline.

6. A method according to claim 1, wherein said tetracycline derivative is administered systemically.

7. A method according to claim 6, wherein said tetracycline derivative is administered systemically by a controlled release delivery system.

8. A method according to claim 1, wherein said tetracycline derivative is administered orally.

9. A method according to claim 1, wherein said tetracycline derivative is administered topically.

10. A method according to claim 1, wherein said tetracycline derivative is a tetracycline of the formulae selected from the group consisting of:

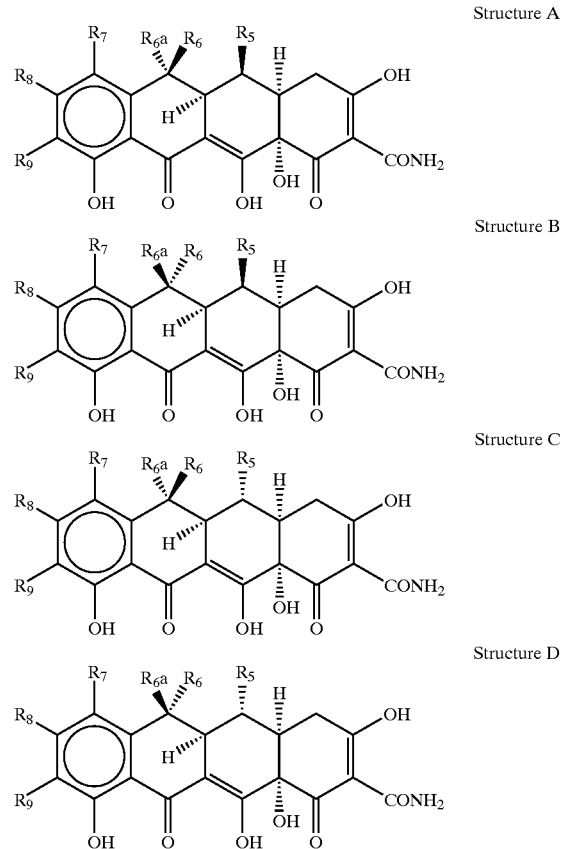

wherein:
R7 is selected from the group consisting of hydrogen, amino, nitro, halogen, ethoxythiocarbonylthio, azido, acylamino, diazonium, cyano, and hydroxyl;

R6-a is selected from the group consisting of hydrogen and methyl;

R6 and R5 are selected from the group consisting of hydrogen and hydroxyl;

R8 is selected from the group consisting of hydrogen and halogen;

R9 is selected from the group consisting of hydrogen, amino, azido, nitro, acylamino, hydroxy, ethoxythiocarbonylthio, halogen, diazonium and RCH(NH$_2$)CO; R is hydrogen;

and pharmaceutically acceptable salts thereof; with the following provisos:

when either R7 and R9 are hydrogen then R8 must be halogen; and when R6-a, R6, R5 and R9 are all hydrogen and R7 is hydrogen, amino, nitro, halogen, dimethylamino or diethylamino, then R8 must be halogen; and when R6-a is methyl, R6 and R9 are both hydrogen, R5 is hydroxyl, and R7 is hydrogen, amino, nitro, halogen or diethylamino, then R8 is halogen; and when R6-a is methyl, R6 is hydroxyl, R5, R7 and R9 are all hydrogen, then R8 must be halogen; and when R6-a, R6 and R5 are all hydrogen, R9 is methylamino and R7 is dimethylamino, then R8 must be halogen; and when R6-a is methyl, R6 is hydrogen, R5 is hydroxyl, R9 is methylamino and R7 is dimethylamino, then R8 must be halogen; and when R6-a is methyl, R6, R5 and R9 are all hydrogen and R7 is cyano, then R8 must be halogen.

11. A method according to claim 1, wherein said tetracycline derivative is a tetracycline compound of the formulae selected from the group consisting of:

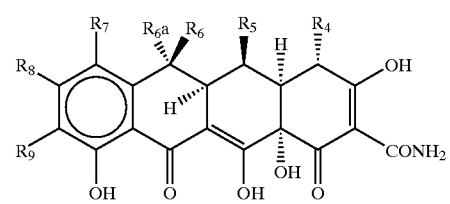

Structure E

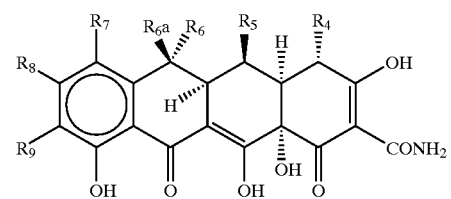

Structure F

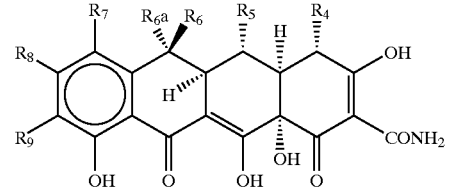

Structure G

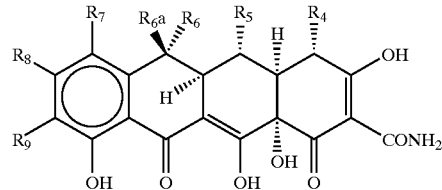

Structure H wherein:

R7 is selected from the group consisting of hydrogen, amino, nitro, halogen, ethoxythiocarbonylthio, azido, acylamino, diazonium, cyano, and hydroxyl;

R6-a is selected from the group consisting of hydrogen and methyl;

R6 and R5 are selected from the group consisting of hydrogen and hydroxyl;

R4 is NOH;

R8 is selected from the group consisting of hydrogen and halogen;

R9 is selected from the group consisting of hydrogen, amino, azido, nitro, acylamino, hydroxy, ethoxythiocarbonylthio, halogen, and RCH(NH$_2$)CO;

R is hydrogen;

and pharmaceutically acceptable salts thereof; with the following provisos:

when R4 is NOH, and R7, R6-a, R6, R5, and R9 are all hydrogen, then R8 must be halogen; and when R4 is NOH, R6-a is methyl, R6 is hydrogen or hydroxyl, R7 is halogen, R5 and R9 are both hydrogen, then R8 must be halogen.

12. A method according to claim 1, wherein said tetracycline derivative is a 4-dedimethylaminotetracycline compound of the formulae selected from the group consisting of

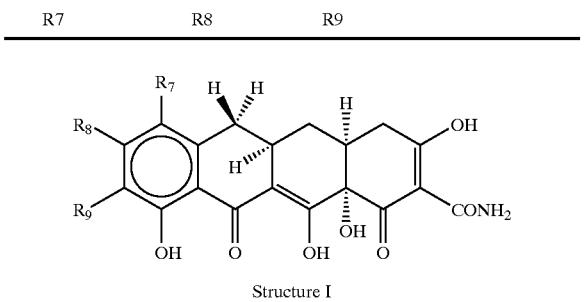

Structure I wherein: R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| dimethylamino | hydrogen | diazonium |

-continued

| R7 | R8 | R9 |
|---|---|---|
| dimethylamino | chloro | amino |
| hydrogen | chloro | amino |
| amino | chloro | amino |
| acylamino | chloro | acylamino |
| amino | chloro | hydrogen |
| acylamino | chloro | hydrogen |
| nitro | chloro | amino |
| dimethylamino | chloro | acylamino |
| dimethylamino | chloro | dimethylamino | and

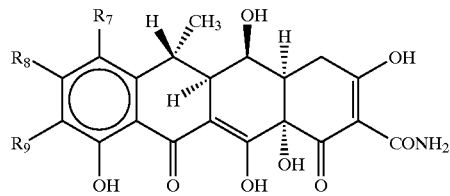

Structure J

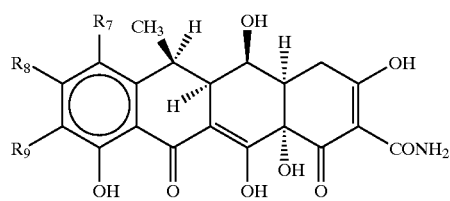

Structure K

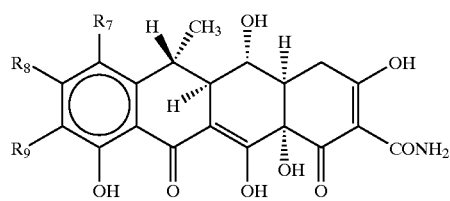

Structure L

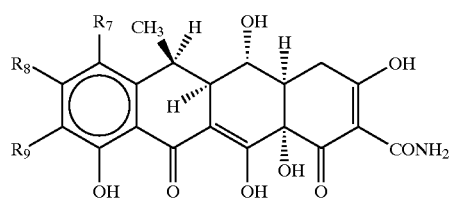

Structure M wherein: R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| hydrogen | hydrogen | diazonium |
| hydrogen | hydrogen | dimethylamino |
| diazonium | hydrogen | hydrogen |
| ethoxythiocarbonylthio | hydrogen | hydrogen |
| dimethylamino | chloro | amino |
| amino | chloro | amino |
| acylamino | chloro | acylamino |
| hydrogen | chloro | amino |
| amino | chloro | hydrogen |
| acylamino | chloro | hydrogen |
| nitro | chloro | amino | and

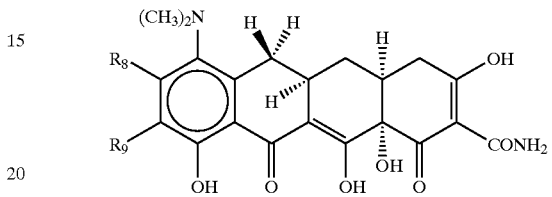

Structure N wherein: R8 is hydrogen or halogen and R9 is selected from the group consisting of nitro, (N,N-dimethyl)glycylamino, and ethoxythiocarbonylthio; and

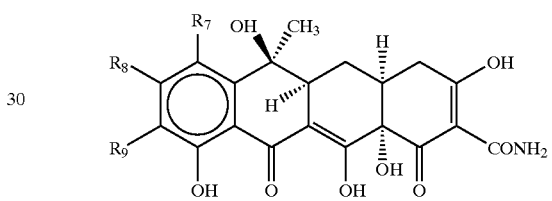

Structure O

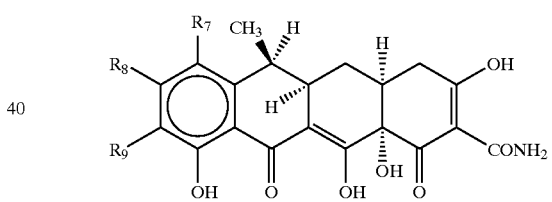

Structure P wherein: R7, R8, and R9 taken together in each case, have the following meanings:

| R7 | R8 | R9 |
|---|---|---|
| amino | hydrogen | hydrogen |
| nitro | hydrogen | hydrogen |
| azido | hydrogen | hydrogen |
| dimethylamino | hydrogen | azido |
| hydrogen | hydrogen | amino |
| hydrogen | hydrogen | azido |
| hydrogen | hydrogen | nitro |
| bromo | hydrogen | hydrogen |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| diethylamino | hydrogen | hydrogen |
| hydrogen | hydrogen | ethoxythiocarbonylthio |
| dimethylamino | hydrogen | methylamino |
| dimethylamino | hydrogen | acylamino |
| dimethylamino | chloro | amino |
| amino | chloro | amino |
| acylamino | chloro | acylamino |
| hydrogen | chloro | amino |
| amino | chloro | hydrogen |

-continued

| R7 | R8 | R9 |
|---|---|---|
| acylamino | chloro | hydrogen |
| nitro | chloro | amino | and pharmaceutically acceptable salts thereof.

13. A method of reducing the risk of cataract development in a mammal in need thereof comprising administering to the mammal an effective amount of minocycline.

14. A method according to claim 13, wherein said minocycline is administered systemically.

15. A method according to claim 14, wherein said minocycline is administered systemically by a controlled release delivery system.

16. A method according to claim 13, wherein said minocycline is administered orally.

17. A method according to claim 13, wherein said minocycline is administered topically.

18. A method according to claim 13, wherein said minocycline is administered in an amount that is effective to reduce the risk of cataract development in the mammal but has substantially no antibacterial activity.

19. A method of reducing the risk of cataract development in a mammal in need thereof comprising administering to the mammal an effective amount of doxycycline.

20. A method according to claim 19, wherein said doxycycline is administered systemically.

21. A method according to claim 20, wherein said doxycycline is administered systemically by a controlled release delivery system.

22. A method according to claim 19, wherein said doxycycline is administered orally.

23. A method according to claim 19, wherein said doxycycline is administered topically.

24. A method according to claim 19, wherein said doxycycline is administered in an amount that is effective to reduce the risk of cataract development in the mammal but has substantially no antibacterial activity.

25. A method of reducing the risk of cataract development in a mammal comprising administering to the mammal in need thereof an effective amount of tetracycline wherein said tetracycline is administered systemically or orally, in an amount that is effective to reduce the risk of cataract development in a mammal but has substantially no antibacterial activity.

* * * * *

UNITED STATES PATENT AND TRADEMARK OFFICE
CERTIFICATE OF CORRECTION

PATENT NO. : 6,914,057 B1
DATED : July 5, 2005
INVENTOR(S) : Ryan et al.

It is certified that error appears in the above-identified patent and that said Letters Patent is hereby corrected as shown below:

<u>Column 1,</u>
Lines 10-12, please replace with the following:
-- This invention was made with support from the United States Government under Grant No. K11 DE-00363 awarded by the National Institutes of Health. The United States government has certain rights in this invention. --.

Signed and Sealed this

Sixth Day of September, 2005

JON W. DUDAS
*Director of the United States Patent and Trademark Office*